(12) United States Patent
Owens et al.

(10) Patent No.: US 11,890,413 B2
(45) Date of Patent: Feb. 6, 2024

(54) TRACHCOLLAR SAFETY ALARM

(71) Applicants: Dorothy Owens, Erial, NJ (US); Darleen Sawyer, Pennsauken, NJ (US)

(72) Inventors: Dorothy Owens, Erial, NJ (US); Darleen Sawyer, Pennsauken, NJ (US)

(73) Assignee: Innovations Unlimited, LLC, Pennsauken, NJ (US)

( * ) Notice: Subject to any disclaimer, the term of this patent is extended or adjusted under 35 U.S.C. 154(b) by 423 days.

(21) Appl. No.: 17/099,046

(22) Filed: Nov. 16, 2020

(65) Prior Publication Data

US 2021/0146073 A1     May 20, 2021

Related U.S. Application Data

(60) Provisional application No. 62/974,105, filed on Nov. 14, 2019.

(51) Int. Cl.
    *A61M 16/00*     (2006.01)
    *A61M 16/04*     (2006.01)

(52) U.S. Cl.
CPC .... *A61M 16/0051* (2013.01); *A61M 16/0003* (2014.02); *A61M 16/021* (2017.08); *A61M 16/0402* (2014.02); *A61M 16/0465* (2013.01); *A61M 2205/18* (2013.01); *A61M 2205/581* (2013.01); *A61M 2205/584* (2013.01); *A61M 2205/587* (2013.01); *A61M 2205/8206* (2013.01)

(58) Field of Classification Search
CPC ............ A61M 16/047; A61M 16/0465; A61M 16/0497
See application file for complete search history.

(56) References Cited

U.S. PATENT DOCUMENTS 3,595,228 A     7/1971     Simon
4,259,965 A     4/1981     Fukuda
(Continued)

FOREIGN PATENT DOCUMENTS

WO     2014078751 A1     5/2014
WO     2017222748 A1     12/2017

OTHER PUBLICATIONS

Written Opinion, dated Dec. 31, 2020 for corresponding PCT Application No. PCT/US20/60721, International Filing Date Nov. 16, 2020, consisting of 7 pages.
(Continued)

*Primary Examiner* — Samchuan C Yao
*Assistant Examiner* — Tina Zhang

(57) ABSTRACT

A device to monitor movement of a tracheostomy tube is described. The device includes a faceplate that is releasably attached to a tracheostomy collar such that the faceplate may be used without the tracheostomy collar. The tracheostomy collar includes a sensor component and an actuator component each located proximate the faceplate. The actuator component actuates when the sensor component moves from a first position to a second position. The second position is further from the actuator component than the first position. The sensor component transmits a signal to an alarm assembly in response to the actuator component actuating. The alarm assembly produces an alert in response to receiving the signal from the sensor component.

18 Claims, 15 Drawing Sheets

(56) References Cited

U.S. PATENT DOCUMENTS

| | | | |
|---|---|---|---|
| 4,270,529 A * | 6/1981 | Muto | A61M 16/0493 128/200.26 |
| 5,578,003 A | 11/1996 | Borger | |
| 6,105,577 A | 8/2000 | Varner | |
| 6,588,426 B2 | 7/2003 | Linderoth | |
| 6,725,862 B2 | 4/2004 | Klinberg | |
| 6,994,088 B2 | 2/2006 | Briggs, III | |
| 7,416,532 B1 | 8/2008 | Broshears | |
| 7,874,999 B2 | 1/2011 | Busby | |
| 9,195,799 B2 | 11/2015 | Sze | |
| 9,358,357 B2 | 6/2016 | Jatana | |
| 9,788,583 B1 * | 10/2017 | Owens | A41D 13/1245 |
| 10,220,169 B2 | 3/2019 | Freeman | |
| 2005/0161047 A1 | 7/2005 | Briggs | |
| 2006/0174893 A1 | 8/2006 | Kanowitz | |
| 2007/0062540 A1 * | 3/2007 | Murray-Harris | A61M 16/047 128/207.14 |
| 2010/0256482 A1 * | 10/2010 | Peters | A61M 16/0486 600/424 |
| 2011/0031961 A1 * | 2/2011 | Durand | A61B 5/06 324/207.2 |
| 2011/0133936 A1 * | 6/2011 | Sanchez | G16Z 99/00 340/691.1 |
| 2012/0167882 A1 | 7/2012 | Wood | |
| 2012/0222682 A1 | 9/2012 | Nguyen | |
| 2013/0213405 A1 | 8/2013 | Dillworth | |
| 2013/0233322 A1 | 9/2013 | Jatana | |
| 2013/0255691 A1 | 10/2013 | Mansfield | |
| 2014/0014095 A1 * | 1/2014 | Morris | A61M 16/0465 128/200.26 |
| 2015/0235570 A1 * | 8/2015 | Quail | G09B 23/28 434/262 |
| 2015/0283351 A1 | 10/2015 | Castello | |
| 2015/0297866 A1 | 10/2015 | Hyman | |
| 2016/0114142 A1 | 4/2016 | Ziaie | |
| 2016/0250466 A1 | 9/2016 | Boggs, II | |
| 2016/0287827 A1 | 10/2016 | Bonutti | |
| 2017/0252198 A1 | 9/2017 | Thorsteinsdottir | |
| 2018/0153506 A1 * | 6/2018 | Rodriquez | A61H 31/00 |
| 2019/0232004 A1 * | 8/2019 | Conrad | A61M 16/022 |
| 2022/0249032 A1 * | 8/2022 | Devarasetty | A61B 5/165 |

OTHER PUBLICATIONS

International Search Report, dated Feb. 8, 2021 for corresponding PCT Application No. PCT/US20/60721, International Filing Date Nov. 16, 2020, consisting of 2 pages.

* cited by examiner

TRACHCOLLAR SAFETY ALARM

CROSS-REFERENCE TO RELATED APPLICATIONS

This application is a U.S. Non-Provisional Patent Application that claims priority from U.S. Provisional Patent Application No. 62/974,105, filed on Nov. 14, 2019, the contents of which are hereby fully incorporated by reference.

FIELD OF THE EMBODIMENTS

The field of the invention and its embodiments relate to a securing collar or band, sensor apparatus, and alarm assemblies with wireless communication technology. More specifically, field of the invention and its embodiments relate to the securing collar or band, the sensor apparatus, and the alarm assemblies with wireless communication technology that secure a tracheostomy tube to a patient's body, detect movement of the tracheostomy tube, and that alert medical personnel of the movement of the tracheostomy tube.

BACKGROUND OF THE EMBODIMENTS

During or after medical procedures, tubes may be inserted into a patient to deliver materials, such as fluids or gasses. As an example, a tracheotomy can be performed on patients who suffer from facial trauma or tumors of the head and/or neck. A tracheotomy, or tracheostomy, is a surgical procedure which consists of making an incision on the anterior aspect of the neck and opening a direct airway through an incision in the trachea. Tracheal tubes allow a patient to breathe without using the patient's nose or mouth.

Specifically, a tracheostomy (or trach) tube is a curved tube that is inserted into a tracheostomy stoma. A commonly used tracheostomy tube consists of three parts: outer cannula with flange (neck plate), inner cannula, and an obturator. The outer cannula holds the tracheostomy open. A neck plate extends from the sides of the outer tube and has holes to attach cloth ties or Velcro strap around the neck. The inner cannula fits inside the outer cannula and has a locking feature to keep it from being coughed out. The obturator is used to insert a tracheostomy tube. More specifically, the obturator fits inside the tube to provide a smooth surface that guides the tracheostomy tube when it is being inserted.

However, at any time, the tracheal tube can become dislodged, removed, or displaced from the patient inadvertently by the caregiver or patient. Patients who have undergone a tracheostomy require the tracheal tube to be securely and comfortably attached to their neck over long periods of time. Inadvertent removal or displacement of such tubes can be particularly serious to the point that the patient no longer receives the material supplied by the tube. More specifically, removal of such tubes after a tracheotomy can prevent the patient from receiving adequate oxygen, which can lead to serious injury or death.

Thus, what is needed is an apparatus that makes medical tubes more secure and reliable, and therefore less vulnerable to dislodging. Also, what is needed is a method or means to alert a caregiver when a tube is dislodged so that quick and effective corrective action can occur to avoid any injury to the patient.

REVIEW OF RELATED TECHNOLOGY

U.S. Pat. No. 3,595,228 describes a portable alarm device. The portable alarm device is attached to interfitting coupling portions in a therapeutic apparatus, such as, the metal or plastic coupling portions between a respirator hose and tracheostomy tube. The device includes normally engaging electric contacts on the coupling portions which separate with the coupling portions to sense a break. One contact is connected to the patient's body, the other contact connected to a low-power electric pulse generating circuit for triggering an electric switch, the latter being adapted to activate the alarm element when the contacts disconnect to alert hospital personnel.

U.S. Pat. No. 4,259,965 describes a skin electrode for connecting monitoring equipment to the surface of the skin, which is separable into two assemblies: a base assembly adapted to be mounted to the surface of the skin and having a sensing element and a terminal assembly adapted to be releasably coupled with the base assembly and having a lead for connection to the monitoring equipment. The terminal assembly is provided with a magnet while the base assembly is provided with a ferromagnetic element, whereby the releasable coupling and electrical connection of the assemblies may be ensured by the action of the magnet.

U.S. Pat. No. 5,578,003 describes a safety device for blood-, wound secretion- and infusion supplying conduit that leads to a vessel inlet. The safety device includes: a magnet mountable on a conduit, a Reed-relay fixed substantially close to the magnet on a skin of a patient so that when a distance between the Reed-relay and the magnet increases as a result of moving away of the vessel input the Reed-relay is switched, and a device for triggering alarm in response to the switching of the Reed-relay.

U.S. Pat. No. 6,105,577 describes a device for supporting and retaining a tracheostomy tube or an endotracheal tube of the type having a tube, including a flexible support flange and an inner cannula having a locking means which connects the inner cannula to the tube. The device includes a holder base having a uniquely shaped tube receiving opening designed to securely retain the tube therein and which includes at least one through-slot extending outward from the opening for receiving the locking means therethrough and preventing contact between the locking means of the inner cannula and the holder base. The device includes a removable tab which extends into the opening, a removable support strap for releasably securing the holder to the patient and an anchor strap for anchoring a circuit in place.

U.S. Pat. No. 6,588,426 describes achieving unwanted separation of an inner cannula from an outer cannula in tracheostomy devices by installing a retaining ring that prevents the inner cannula from unwantingly being unlatched from the outer cannula. The retaining ring allows the air supply elbow to be separated which, in turn, permits the sensory alarms to properly sound when a disconnection of the air supply arises.

U.S. Pat. No. 7,416,532 describes an alarm device that includes a temperature sensor placed in the tube of a trach tube and which is adapted to activate an audible alarm when predetermine low temperature has been detected.

U.S. Pat. No. 7,874,999 describes an access needle for extracorporeal therapy that is equipped with a mount and a sleeve having a metal or magnetic component at its distal end. The mount includes a sensor for detecting when the distal end is pressed against the mount. The sensor is a hall-effect sensor or a proximity sensor. When therapy is begun, the sleeve is rolled up and urged against the mount, exposing the needle for use with the patient. While the sleeve, and the piece of metal or magnet, remains in contact with the sensor, the needle has not been dislodged and therapy may continue. If the needle is dislodged, the sleeve pushes away from mount, moving the metal or magnet away from the sensor. The sensor notes the dislodgement and sends a signal to alert the patient or a caregiver.

U.S. Pat. No. 6,725,862 describes a measured suction system that utilizes a tracheostomy tube apparatus, including: a tracheostomy tube, a tracheostomy collar, and a swivel adapter. The tracheotomy tube includes an internal channel within the tracheostomy tube allowing for all suctioning of the patient. The system will insure that all negative suction pressure is maintained within the tracheostomy tube, which eliminates any trauma that may be caused by using excessive negative suction pressures when the standard methods of suctioning are employed.

U.S. Pat. No. 9,358,357 describes a collar for a tracheostomy tube, a method of securing a tracheostomy tube to the neck of a patient, and a medical device including a collar for the tracheostomy tube. In one exemplary embodiment, the collar includes a securing portion, a protection portion, and an attachment portion. The securing portion secures the tracheostomy tube to the neck of the patient. The protection portion extends from the securing portion and covers a portion of a flange of the tracheostomy tube. The protection portion is also positioned between the tracheostomy tube flange and the neck skin of the patient when the securing portion is attached to the tracheostomy tube. The attachment portion attaches the securing portion to the tracheostomy tube.

U.S. Pat. No. 9,195,799 describes a patient monitoring system for monitoring vital signs. The system comprises: one or more sensors that measure vital signs, a monitor station, and one or more portable monitoring devices. The monitored data based on the measured vital signs is wirelessly transmitted from the sensors to the monitor station. The monitor station issues one or more alarms to certain ones of the portable monitoring devices as a function of the monitored data. A portion of the monitored data that pertains to the alarms is wirelessly transmitted to the certain ones of the portable monitoring devices and displayed by the certain ones of the portable monitoring devices.

U.S. Pat. No. 6,994,088 describes a retainer comprising a ring configured to fit over a readily available tracheostomy tube and be securable thereto, and further having cooperating straps configured to extend around and secure an auxiliary device coupled to the tracheostomy tube, such as a ventilator tube. The retainer is configured to be selectively and easily attachable to existing tracheostomy tubes to provide a platform for securing an auxiliary device.

U.S. Pat. No. 10,220,169 describes a ventilation monitoring device that comprises at least one processor and at least one memory including computer program code. The at least one memory and the computer program code is configured with the at least one processor to cause the ventilation monitoring device to determine whether an intubated subject's tracheal tube is properly placed by receiving an indication of a subject's breath from at least one sensor.

U.S. Published Patent Application No. 2013/0213405 describes a ventilator tube holder. The ventilator tube holder is in the form of a soft patch having opposed ends which are Velcroed to underlying tracheostomy ties, with a central portion having a circular orifice through which the ventilator tube passes and is held. In one embodiment the circular orifice is provided with a notch or slit for easy mounting of the patch around the ventilator tube or for quick removal of the ventilator tube, whereas in a further embodiment a soft elastic tie or strip is Velcroed from one side of the orifice to the other to hold the ventilator tube in place or to tighten the ventilator tube to the patch during any kind of deformation or stretching that may occur.

U.S. Published Patent Application No. 2013/0255691 relates to a system and method for use of acoustic reflectometry information in ventilation devices. The system and method includes a speaker to emit sound waves into an intubated endotracheal tube ("ETT") and a microphone to detect returning acoustic reflections. In addition, the system and method includes a reflectometry device in communication with a ventilation device for analyzing timings and amplitudes of the returning acoustic reflections to determine a size of a passageway around an ETT tip, location and size of ETT obstructions, and relative movement of the ETT tip within a trachea. The reflectometry device is also configured to determine a resistance parameter representative of resistance to actual flow of air through the ETT based upon a function of the diameter of the ETT, length of the ETT, and percent obstruction of the ETT, where the resistance parameter is used to calculate the tracheal pressure.

U.S. Published Patent Application No. 2015/0283351 provides a medical device for monitoring breathing of a patient. The device includes an adapter with at least one port, a monitor, and at least one tubing connecting the at least one port and the monitor. The adapter is attached to a tracheostomy tube.

U.S. Published Patent Application No. 2015/0297866 provides catheter securement devices that can be used to secure catheters, catheter hubs, and ether medical devices to the body of a patient. The catheter securement devices can include an adhesive pad and engagement tabs with a slide locking feature. Adaptors can be used to provide suture tabs to catheters that lack suture tabs.

U.S. Published Patent Application No. 2016/0114142 provides a remotely activatable capsule. The capsule includes a housing that can be swallowed by a subject, an electrical energy reservoir having a first terminal and a second terminal positioned in the housing, a remotely activatable switch positioned in the housing and configured to be remotely activated, and a function-specific mechanism positioned in the housing and electrically coupled to the remotely activatable switch and to the electrical energy reservoir and configured to perform a function when the remotely activatable switch is activated.

U.S. Published Patent Application No. 2016/0250466 provides neurostimulation assemblies, systems, and methods that make possible the providing of short-term therapy or diagnostic testing by providing electrical connections between muscles and/or nerves inside the body and stimulus generators and/or recording instruments mounted on the surface of the skin or carried outside the body.

U.S. Published Patent Application No. 2012/0222682 provides a tracheostomy tube securer that includes a band with a first set of apertures and a strap with a second set of apertures. Tracheostomy tube securer further comprises a band thread and a strap thread to lace through the sets of apertures. Tracheostomy tube securer further comprises a tab for quick release of the securing system in an emergency situation.

U.S. Published Patent Application No. 2017/0252198 describes a cervical collar that has a chin support slidably connected to an inside surface of an anterior component adapted to secure against an anterior chin and neck of a user. A posterior component connects to the anterior component to circumferentially surround the user's neck. A height adjustment mechanism has spring locks securing the height adjustment mechanism against the anterior component. The cervical collar includes a footplate continuously extending from the height adjustment mechanism generally without a variation in thickness. The posterior component has side portions with a plurality of living hinges located proximate to elongate slots for straps connecting to the anterior component.

U.S. Published Patent Application No. 2016/0287827 describes a system for determining a position of a medical device in a respiratory system of a patient. The system includes a positioning apparatus and a flexible guide rod having a distal portion. The flexible guide rod is configured to be inserted into a passage of the respiratory system of the patient through the positioning apparatus. The system also includes an emitter coupled to the distal portion of the flexible guide rod. The system includes a flexible guide tube, covering the flexible guide rod, and configured to move together with the guide rod through the positioning apparatus and the respiratory system of the patient. The guide rod can be removed through the guide tube and positioning apparatus, leaving a passage into the respiratory system of the patient through the guide tube. Further, a magnet external to the patient is provided, where the magnet is configured to create a magnetic field in the patient. Moreover, the system includes at least three sensors positioned external to the patient. The at least three sensors are configured to interact with the emitter positioned on the distal portion of the guide rod and the magnetic field created in the patient by the magnet. The system also includes a display screen, a computer connected to the display screen, and the at least three sensors external to the patient. The position of the emitter at the distal portion of the guide rod, relative to the respiratory system of the patient, is configured to be detected by at least one of the at least three sensors external to the patient, output to the computer, and indicated on the display screen in a schematic representation of the respiratory system of the patient.

U.S. Published Patent Application No. 2012/0167882 describes an intubation system that includes a tracheal tube, a heat source coupled to the tracheal tube, and a temperature sensor disposable in a patient's trachea to detect a temperature within the patient's trachea. The heat source is adapted to generate heat when the tracheal tube is disposed in the airway of the patient. A temperature control system coupled to the heat source is adapted to monitor the detected temperature and to control generation of heat from the heat source based on the detected temperature.

WO 2014/078751 A1 provides a medical device for monitoring breathing of a patient that comprising an adapter with at least one port; a monitor; and at least one tubing connecting the at least one port and the monitor wherein the adapter attached to a tracheostomy tube.

Various tracheostomy collars and alarm devices are known in the art. However, their means of operation are substantially different from the present disclosure, as the other inventions fail to solve all the problems taught by the present disclosure.

SUMMARY OF THE EMBODIMENTS

The present invention and its embodiments relate to a securing collar or band, sensor apparatus, and alarm assemblies with wireless communication technology. More specifically, the present invention and its embodiments relate to securing collar or band, the sensor apparatus, and the alarm assemblies with wireless communication technology that secure a tracheostomy tube to a patient's body, detect movement of the tracheostomy tube, and that alert medical personnel of the movement of the tracheostomy tube.

A first embodiment of the present invention describes a device configured to monitor movement of a tracheostomy tube. The device includes a faceplate and a tracheostomy collar. The faceplate is releasably attached to a tracheostomy collar such that the faceplate may be used without the tracheostomy collar. The faceplate includes a body and a first end disposed opposite a second end. The body includes an opening disposed therethrough. The opening receives a portion of a tracheostomy tube therein. The first end of the faceplate includes a first aperture and the second end of the faceplate includes a second aperture.

The tracheostomy collar includes a main body having a first end and a second end. The first end of the tracheostomy collar includes a first attachment means receivable through the first aperture and the second end of the tracheostomy collar includes a second attachment means receivable through the second aperture. The tracheostomy collar also includes a sensor component and an actuator component each located proximate the faceplate.

The actuator component is configured to actuate when the sensor component moves from a first position to a second position, from the first position to a third position, and from the first position to a fourth position. The first position, the second position, the third position, and the fourth position differ. More specifically, the second position is further from the actuator component than the first position. The third position is further from the actuator component than the first position and the second position. The fourth position is further from the actuator component than the first position, the second position, and the third position.

Additionally, the sensor component is configured to transmit a signal to an alarm assembly in response to the actuator component actuating. The alarm assembly is configured to produce an alert in response to receiving the signal from the sensor component.

The alarm assembly also includes alarm circuitry, a battery, and/or a transmitter configured to transmit an audio signal and/or a visual signal to an electronic device in response to the production of the alert. In other examples, the alarm assembly further includes a speaker configured to produce an audio alert in response to the production of the alert. In some examples, the alarm assembly includes one or more indicators. Each of the one or more indicators comprises a light-emitting diode (LED). A first indicator of the one or more indicators emits a first color of light. A second indicator of the one or more indicators emits a second color of light. A third indicator of the one or more indicators emits a third color of light. The first color of light, the second color of light, and the third color of light differ.

In response to the actuator component actuating when the sensor component moves from the first position to the second position, the first indicator emits the first color of light. In response to the actuator component actuating when the sensor component moves from the first position to the third position, the second indicator emits the second color of light. Further, in response to the actuator component actuating when the sensor component moves from the first position to the fourth position, the third indicator emits the third color of light.

A second embodiment of the present invention describes a system that monitors movement of a tracheostomy tube. The system includes a network, an electronic device, and a device. The device is configured to prevent movement of a tracheostomy tube. The device includes a faceplate and a tracheostomy collar. The faceplate is releasably attached to a tracheostomy collar such that the faceplate may be used without the tracheostomy collar. The faceplate includes a body and a first end disposed opposite a second end. The body includes an opening disposed therethrough. The opening receives a portion of a tracheostomy tube therein. The first end of the faceplate includes a first aperture and the second end of the faceplate includes a second aperture.

The tracheostomy collar includes a main body having a first end and a second end. The first end of the tracheostomy collar includes a first attachment means receivable through the first aperture and the second end of the tracheostomy collar includes a second attachment means receivable through the second aperture. The tracheostomy collar also includes a sensor component and an actuator component each located proximate the faceplate.

The actuator component is configured to actuate when the sensor component moves from a first position to a second position, from the first position to a third position, and from the first position to a fourth position. The first position, the second position, the third position, and the fourth position differ. More specifically, the second position is further from the actuator component than the first position. The third position is further from the actuator component than the first position and the second position. The fourth position is further from the actuator component than the first position, the second position, and the third position.

Additionally, the sensor component is configured to transmit a signal to an alarm assembly in response to the actuator component actuating. The alarm assembly is configured to produce an alert in response to receiving the signal from the sensor component.

The alarm assembly also includes a speaker configured to produce an audio alert in response to the production of the alert. Moreover, the alarm assembly includes one or more indicators, where each of the one or more indicators comprises an LED. A first indicator of the one or more indicators emits a first color of light. A second indicator of the one or more indicators emits a second color of light. A third indicator of the one or more indicators emits a third color of light. The first color of light, the second color of light, and the third color of light differ.

In response to the actuator component actuating when the sensor component moves from the first position to the second position, the first indicator emits the first color of light. In response to the actuator component actuating when the sensor component moves from the first position to the third position, the second indicator emits the second color of light. Further, in response to the actuator component actuating when the sensor component moves from the first position to the fourth position, the third indicator emits the third color of light.

A third embodiment of the present invention describes a method to monitor movement of a tracheostomy tube. The method includes numerous process steps, such as: affixing a tracheostomy tube to a patient and attaching a device configured to prevent movement of the tracheostomy tube to the patient. The device comprises a faceplate and a tracheostomy collar. The faceplate is releasably attached to a tracheostomy collar such that the faceplate may be used without the tracheostomy collar. The tracheostomy collar comprises: an actuator component and a sensor component located proximate the faceplate, an alarm assembly, and/or a transmitter. In response to detecting movement, by the sensor component, from a first position to a second position, from the first position to a third position, and from the first position to a fourth position, the method includes actuating, by the actuator component. The first position, the second position, the third position, and the fourth position differ. The second position is further from the actuator component than the first position. The third position is further from the actuator component than the first position and the second position. The fourth position is further from the actuator component than the first position, the second position, and the third position.

The method further includes: transmitting, by the sensor component, a signal to the alarm assembly in response to the actuation of the actuator component; producing, by the alarm assembly, an alert in response to receiving the signal from the sensor component; and transmitting, by the transmitter, the alert to an electronic device via a network.

In examples, the alarm assembly further comprises one or more indicators, where each of the one or more indicators comprises an LED. A first indicator of the one or more indicators emits a first color of light. A second indicator of the one or more indicators emits a second color of light. A third indicator of the one or more indicators emits a third color of light. The first color of light, the second color of light, and the third color of light differ.

In response to the actuator component actuating when the sensor component moves from the first position to the second position, the method further includes emitting, by the first indicator, the first color of light. In response to the actuator component actuating when the sensor component moves from the first position to the third position, the method further includes emitting, by the second indicator, the second color of light. Further, in response to the actuator component actuating when the sensor component moves from the first position to the fourth position, the method further includes emitting, by the third indicator, the third color of light.

In general, the present invention succeeds in conferring the following benefits and objectives.

The present invention provides a device that is configured to prevent movement of a tracheostomy tube.

The present invention provides a device that is configured to monitor, detect, and report movement of a tracheostomy tube to reduce injury or harm to a patient.

The present invention provides a device that is configured to produce an alert in response to detecting movement of a tracheostomy tube.

The present invention provides a device that is to transmit an alarm signal to an electronic device in response to detecting movement of a tracheostomy tube.

DESCRIPTION OF THE PREFERRED EMBODIMENTS

Figure 1:
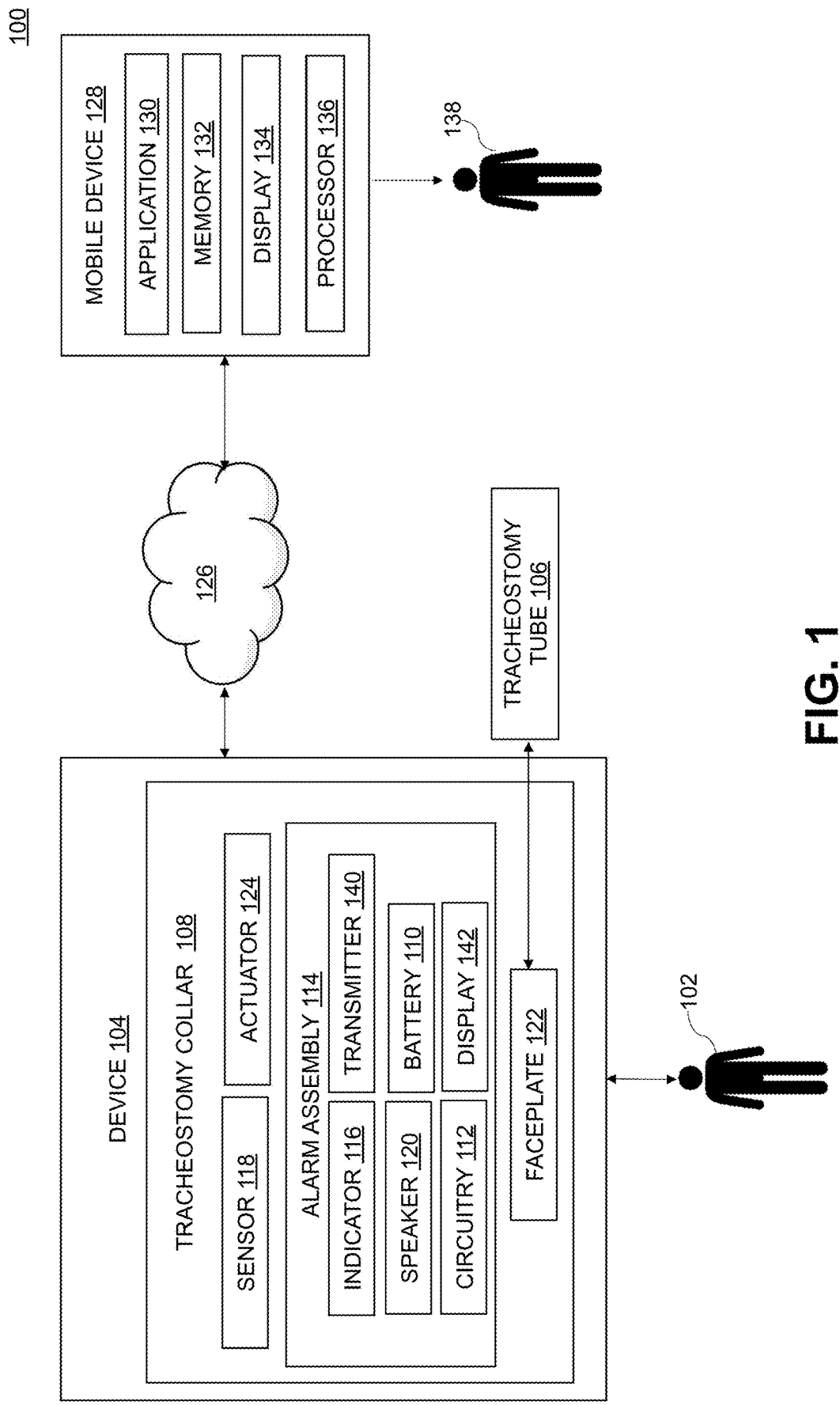
FIG. 1 depicts a block diagram of a system, according to at least some embodiments disclosed herein.

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

FIG. 1 depicts a block diagram of a system 100. The system 100 of FIG. 1 includes a device 104, a network 126 (such as the Internet), and a mobile device 128 (or an electronic device). The device 104 is configured to monitor, detect, and report movement of a tracheostomy tube 106. Moreover, the device 104 is configured to reduce accidental decannulation.

As explained previously, the tracheostomy (or trach) tube 106 is a curved tube that is inserted into a tracheostomy stoma. A commonly used tracheostomy tube consists of three parts: an outer cannula with flange (e.g., a faceplate 122), inner cannula, and an obturator. The outer cannula holds the tracheostomy open. A faceplate 122 extends from the sides of the outer tube and has holes to attach cloth ties or Velcro strap around a neck of the patient 102. The inner cannula fits inside the outer cannula and has a locking feature to keep it from being coughed out. The obturator is used to insert a tracheostomy tube. More specifically, the obturator fits inside the tube to provide a smooth surface that guides the tracheostomy tube when it is being inserted.

Figure 2:
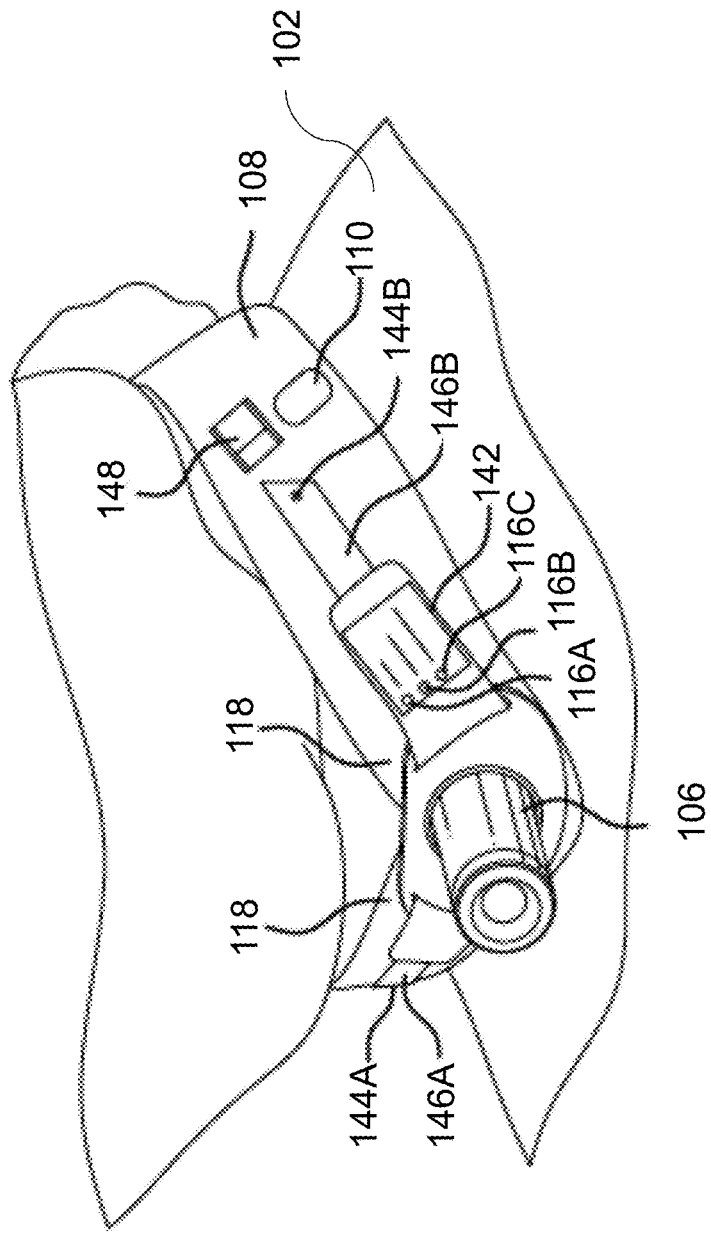
FIG. 2 depicts a perspective view of a device, according to at least some embodiments disclosed herein.
Figure 3:
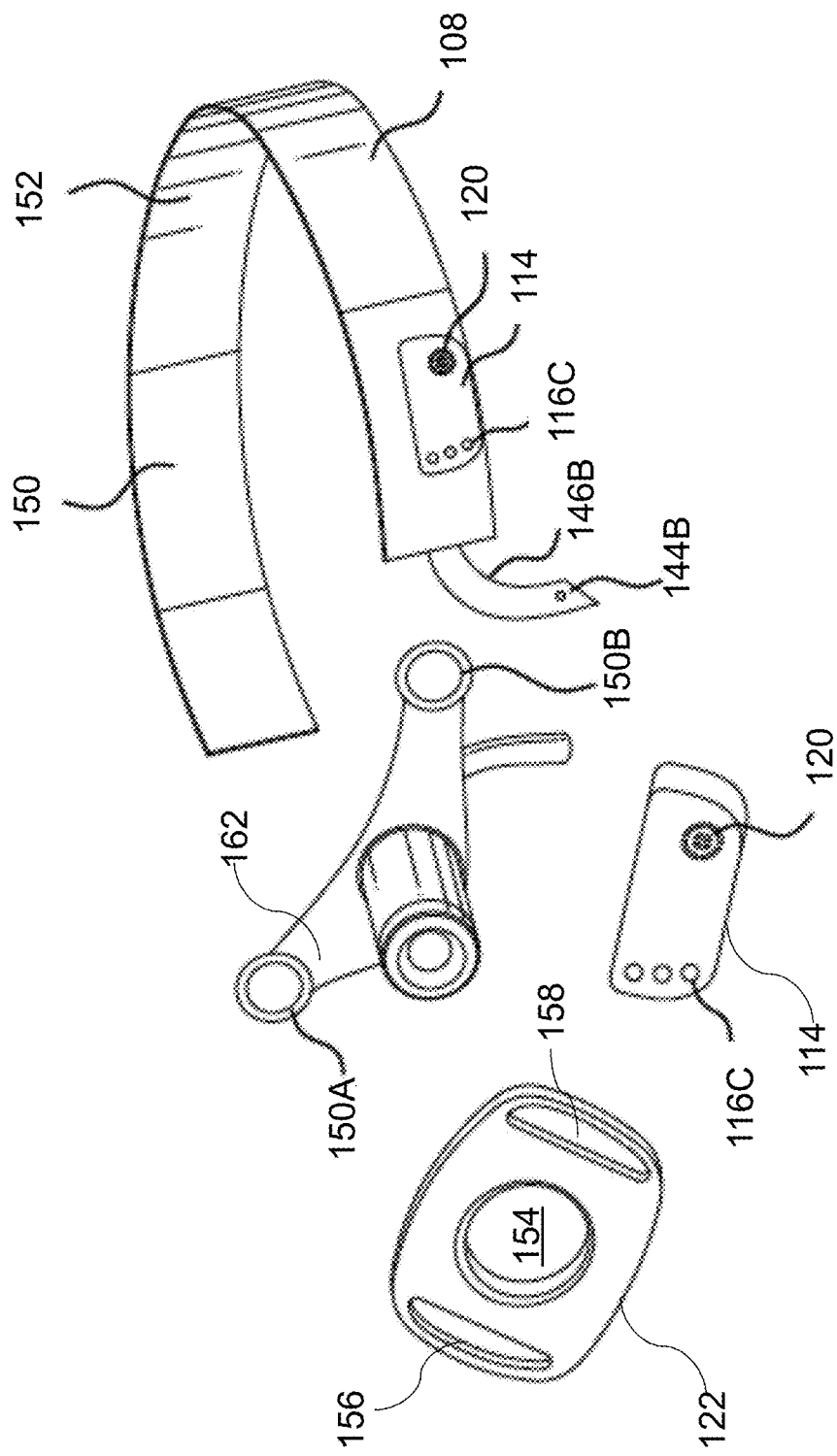
FIG. 3 depicts an exploded view of a device, according to at least some embodiments disclosed herein.

The device 104 includes a tracheostomy collar 108, a portion 162 (of FIG. 2, FIG. 4, and FIG. 5), and the faceplate 122. It should be appreciated that the faceplate 122 is releasably attached to the tracheostomy collar 108 such that the faceplate 122 may be used without the tracheostomy collar 108, in examples. As illustrated in FIG. 3, the faceplate 122 includes a body and a first end disposed opposite a second end. The body of the faceplate 122 includes an opening 154 disposed therethrough. The opening 154 of the faceplate 122 receives a portion of the tracheostomy tube 106 therein. The first end of the faceplate 122 includes a first aperture 156 and the second end of the faceplate 122 includes a second aperture 158.

Moreover, the portion 162 (as shown in FIG. 3) includes an opening disposed therethrough, which is configured to receive a portion of the tracheostomy tube 106 therein. Moreover, the portion 162 includes a first side disposed opposite a second side. The first side of the portion 162 includes a first opening 150A and the second side of the portion 162 includes a second opening 150B.

The tracheostomy collar 108 is releasably attachable to a patient 102. The tracheostomy collar 108 includes a main body having a first end and a second end. As shown in FIG. 2, the first end of the tracheostomy collar 108 includes a first attachment means receivable through the first aperture 156 of the faceplate 122. The second end of the tracheostomy collar 108 includes a second attachment means receivable through the second aperture 158 of the faceplate 122.

In some examples, each of the first attachment means and the second attachment means comprise Velcro 160 (of FIG. 4), securing ties, strips, snaps, buckles, pockets, loops, hooks, clasps, and/or strings, among others. In other examples, each of the first attachment means and the second attachment means may comprise two or more attachment means. In this illustrative example of FIG. 2, each of the first attachment means and the second attachment means may comprise straps and snaps. For example, the first attachment means includes a first strap 146A and a first snap 144A and the second attachment means includes a second strap 146B and a second snap 144B. As shown in at least FIG. 3 and FIG. 4, the first attachment means (e.g., the first strap 146A and the first snap 144A) is first received through the first opening 150A of the first side of the portion 162. Next, the first attachment means is received through the first aperture 156 of the faceplate 122. Moreover, as shown in at least FIG. 3, the second attachment means (e.g., the second strap 146B and the second snap 144B) is first received through the second opening 150B of the second side of the portion 162. Next, the second attachment means is received through the second aperture 158 of the faceplate 122. Then, each of the first attachment means and the second attachment means are affixed to the tracheostomy collar 108. Such affixes the portion 162 between the neck of the patient 102 and the faceplate 122.

Figure 4:
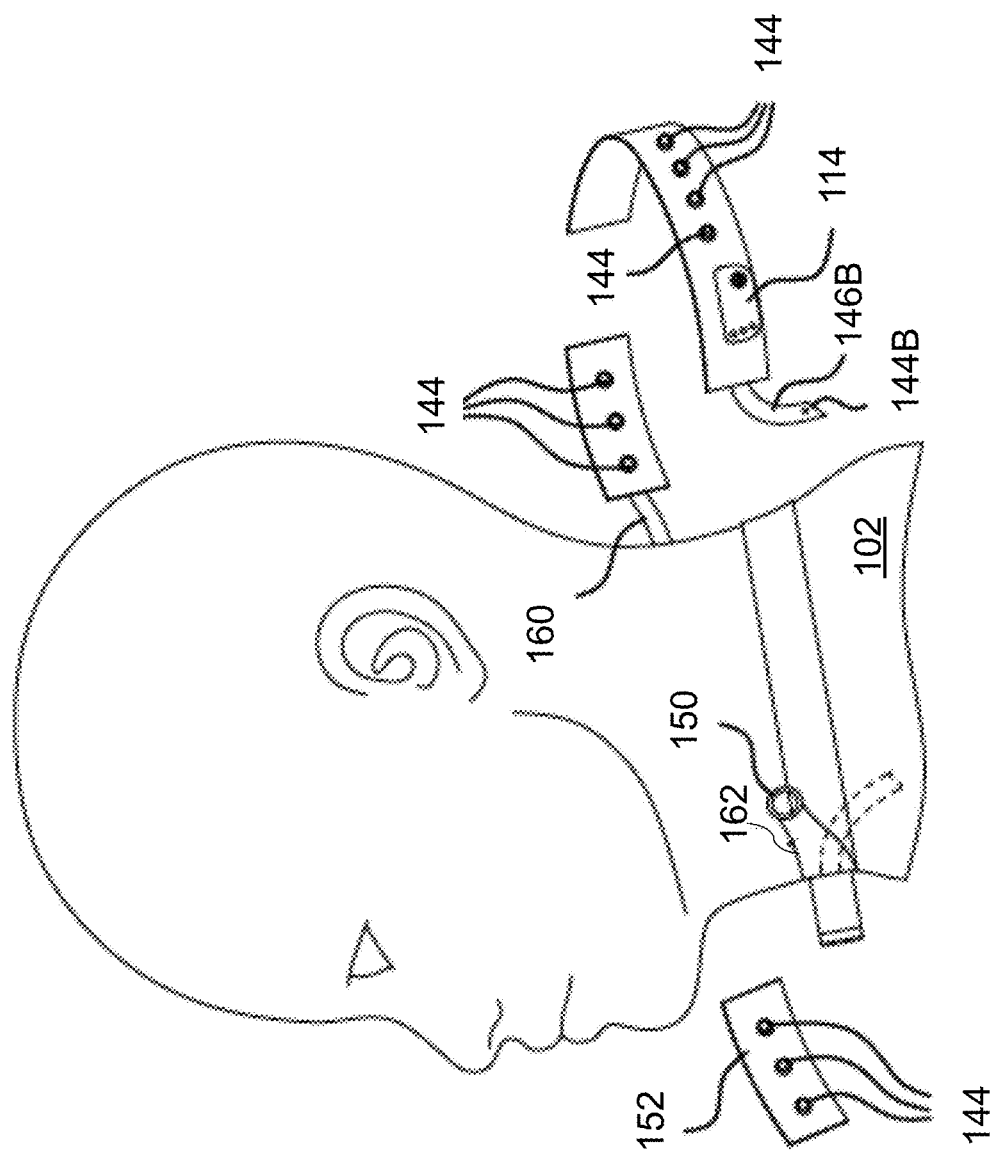
FIG. 4 depicts an exploded view of a device securable to a patient, according to at least some embodiments disclosed herein.
Figure 5:
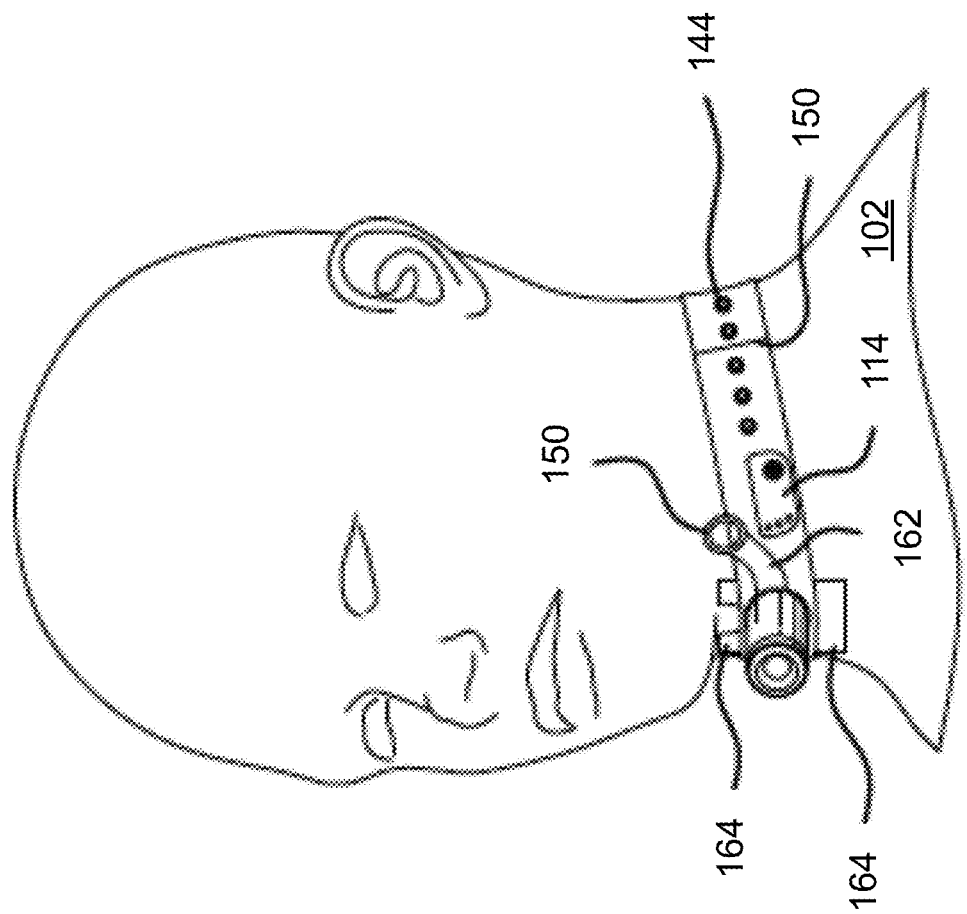
FIG. 5 depicts a perspective view of a device secured to a patient, according to at least some embodiments disclosed herein.
Figure 6:
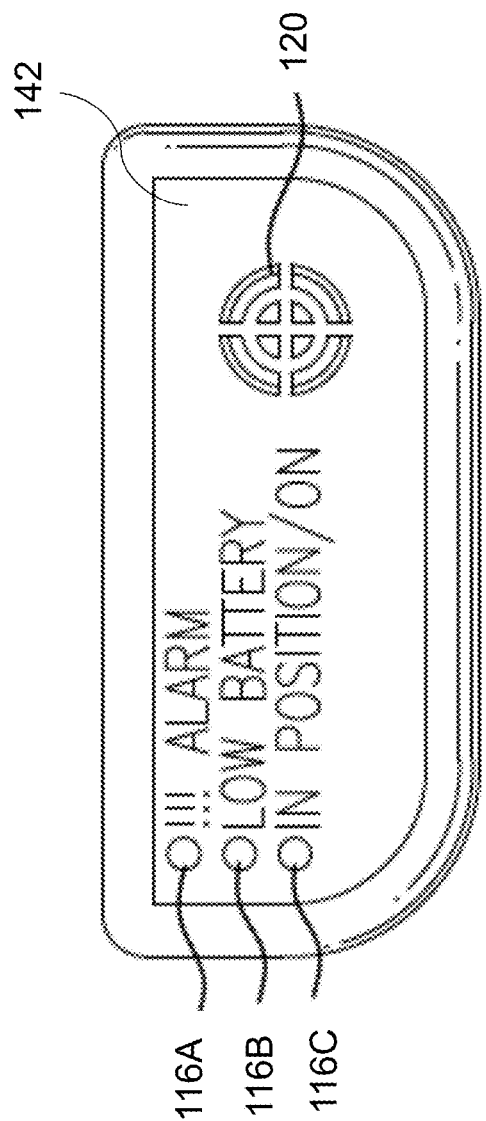
FIG. 6 depicts a perspective view of an alarm assembly of a device, according to at least some embodiments disclosed herein.
Figure 11:
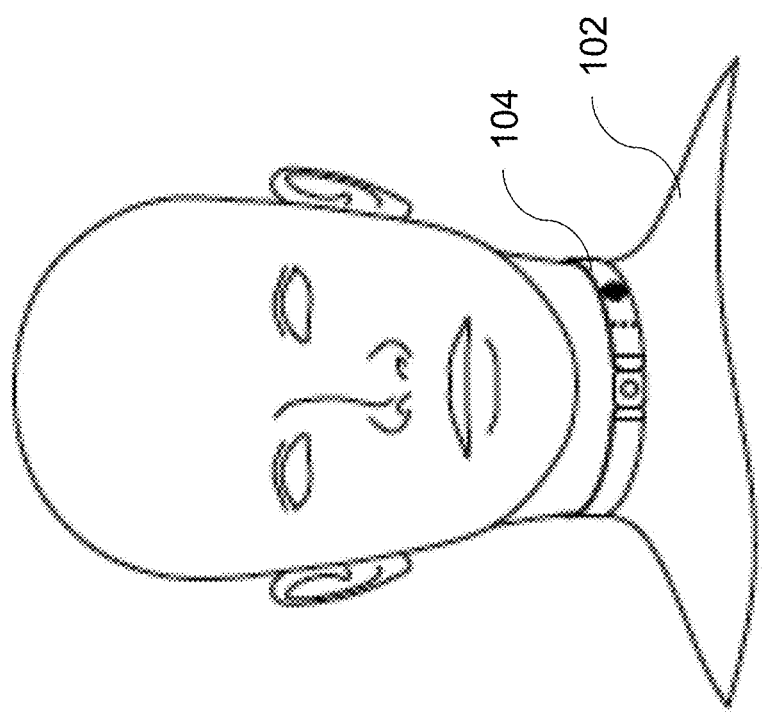
FIG. 11 depicts a perspective view of a device worn by a patient, according to at least some embodiments disclosed herein.
Figure 12:
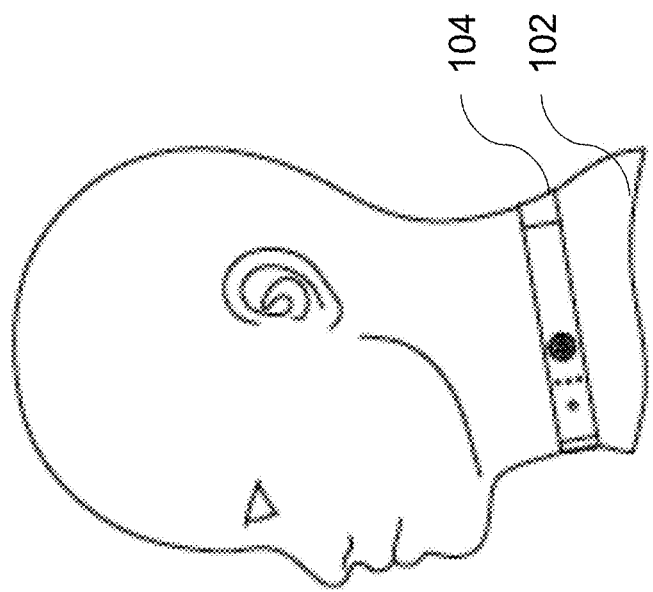
FIG. 12 depicts a side view of a device worn by a patient, according to at least some embodiments disclosed herein.
Figure 13:
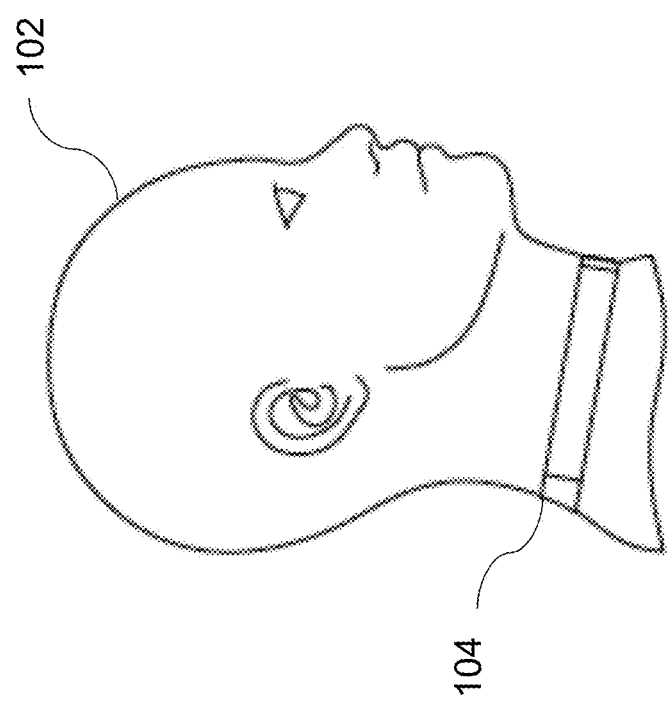
FIG. 13 depicts another side view of a device worn by a patient, according to at least some embodiments disclosed herein.
Figure 14:
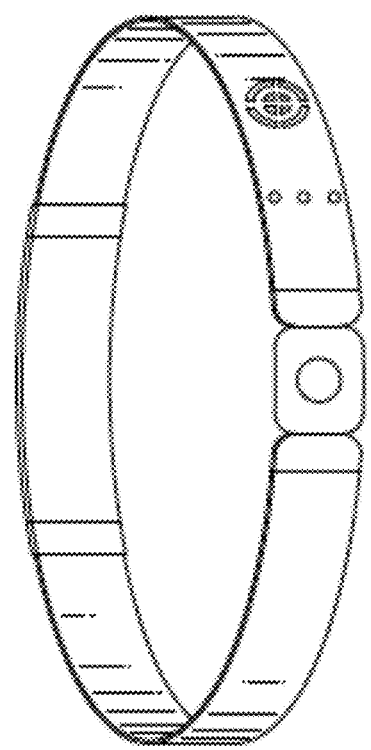
FIG. 14 depicts a perspective view of a device, according to at least some embodiments disclosed herein.

It should further be appreciated that the tracheostomy collar 108 is adjustable in size. As shown in FIG. 3, FIG. 4, and FIG. 5, a first portion 152 of the tracheostomy collar 108 may slide into an opening 150 of the tracheostomy collar 108 to reduce the size of the tracheostomy collar 108. Then, the tracheostomy collar 108 may be snapped (using one or more of the snaps 144 of FIG. 4) or affixed to the desired size. In other examples, excess portions of the tracheostomy collar 108 may be cut and removed. FIG. 11, FIG. 12, and FIG. 13 depict the device 104 affixed to the patient 102.

The tracheostomy collar 108 may comprise one or more materials, such as foam, cotton, or neoprene, among others not explicitly listed herein. It should be appreciated that the one or more materials comprising the tracheostomy collar 108 may be selected such that the one or more materials support the components of the tracheostomy collar 108, protect the patient's skin from moisture, and protect the patient's skin from the faceplate of the device 104 and other components.

Further, the tracheostomy collar 108 comprises numerous components, such as a sensor component 118 (of FIG. 1 and FIG. 2), an actuator component 124 (of FIG. 1), and/or an alarm (or monitoring) assembly 114 (of FIG. 1, FIG. 3, FIG. 4, FIG. 5, FIG. 6, and FIG. 7), among others. It should be appreciated that the components of the tracheostomy collar 108 may be located in a front, a back, or a side of the tracheostomy collar 108 to distribute weight evenly. The sensor component 118 is located under, over, above, beside, or around the faceplate 122 and does not interfere with the tracheostomy tube 106. In preferred examples, the sensor component 118 is located between the faceplate 122 and the neck of the patient 102, as depicted in FIG. 2.

It should be appreciated that the sensor component 118 may be any type of sensor, such as a proximity sensor, a Hall-effect sensor, an infrared sensor, a laser triangulation sensor, a laser distance sensor, a laser displacement sensor, an ultrasonic sensor, a photoelectric sensor, a capacitive sensor, a fiberoptic sensor, a blood oxygenation sensor, an airflow sensor, and/or a reed switch sensor, among others not explicitly listed herein. In other examples, the sensor component 118 may measure one or more physiological parameters of the patient 102, such as a temperature, a heart rate, a respiratory rate, a blood oxygen saturation, an air-flow status, an obstruction status, and/or an end-tidal capnography measurement, etc. In some examples, and as depicted in FIG. 5, the sensor component 118 may be housed in a wound dressing 164.

The actuator component 124 is located under, over, above, beside, or around the faceplate and does not interfere with the tracheostomy tube. In preferred examples, the actuator component 124 is located between the faceplate 122 and the neck of the patient 102. The actuator component 124 is configured to actuate when the sensor component 118 moves from a first position to a second position, from the first position to a third position, and from the first position to a fourth position. The first position, the second position, the third position, and the fourth position differ. It should be appreciated that the second position is further from the actuator component than the first position. The third position is further from the actuator component than the first position and the second position. Additionally, the fourth position is further from the actuator component 124 than the first position, the second position, and the third position.

The sensor component 118 is also configured to transmit a signal to the alarm assembly 114 in response to the actuator component 124 actuating. The alarm assembly 114 of the device 104 is configured to produce an alert in response to receiving the signal from the sensor component 118. The alarm assembly 114 (of FIG. 1, FIG. 3, FIG. 4, FIG. 5, FIG. 6, and FIG. 7) includes numerous components, such as one or more indicators 116 (e.g., a first indicator 116A, a second indicator 116B, and/or a third indicator 116C, among others) (of FIG. 1, FIG. 2, FIG. 3, and FIG. 6), a transmitter 140 (of FIG. 1), a speaker 120 (of FIG. 1, FIG. 3, and FIG. 6), a battery 110 (of FIG. 1, FIG. 2, and FIG. 7), alarm circuitry 112 (of FIG. 1), and/or a display 142 (of FIG. 1, FIG. 2, and FIG. 6), among other components not explicitly listed herein. It should be appreciated that the battery 110 may be rechargeable or non-rechargeable. In some examples, the battery 110 may be replaced with another power source (not shown).

The alarm circuitry 112, in some examples, may be housed in a remote component (not shown). The alarm circuitry 112 of the alarm assembly 114 may include components such as: a general-purpose microprocessor connected to an internal bus. The microprocessor is adapted to execute software, which may include an operating system and one or more applications, as part of performing the functions described herein. A read-only memory (ROM), a random access memory (RAM), the display 142, and the speaker 120 are also connected to the interface bus.

The RAM and ROM are described for illustrative purposes only. Any computer-readable media may be used in the system for data storage. Computer-readable media are capable of storing information that can be interpreted by the microprocessor. This information may be data or may take the form of computer-executable instructions, such as software applications, that cause the microprocessor to perform certain functions and/or computer-implemented methods. Depending on the embodiment, such computer-readable media may comprise computer storage media and communication media. Computer storage media includes volatile and non-volatile, removable and non-removable media implemented in any method or technology for storage of information such as computer-readable instructions, data structures, program modules or other data. Computer storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

The microprocessor of the alarm circuitry 112 may produce the alert in response to receiving the signal from the sensor component 118. In some examples, the display 142 of the alarm assembly 114 may exhibit a list of values that may generally apply to the patient, such as, for example, acceptable movement ranges for the tracheostomy tube 106. The microprocessor may then determine the proper thresholds using the user input data and algorithms stored in the ROM. The patient-specific thresholds may be stored on the RAM for comparison to measured movement of the tracheostomy tube 106. The memory of the alarm assembly 114 also stores user data and information.

The alarm assembly 114 may project visual alerts/alarms and/or audio alerts/alarms in response to receiving the transmitted signal from the sensor component 120. In an example, the speaker 120 of the alarm assembly 114 is configured to produce an audio alert in response to the receiving the transmitted signal from the sensor component 120.

Further, in another example, each of the one or more indicators 116 (e.g., the first indicator 116A, the second indicator 116B, and/or the third indicator 116C) comprise a light-emitting diode (LED). In an illustrative example, a first indicator of the one or more indicators 116 emits a first color of light, a second indicator of the one or more indicators 116 emits a second color of light, and a third indicator of the one or more indicators 116 emits a third color of light. Each of the first, second, and third color may differ. The first color of light may be green (e.g., associated with the tracheostomy tube 106 being in a proper position), the second color of light may be yellow (e.g., associated with a low battery level), and the third color of light may be red (e.g., associated with a high priority level associated with a large amount of movement of the tracheostomy tube 106 that may result in injury to a patient 102 associated with the tracheostomy tube 106). However, the quantity of the one or more indicators 116 and the color of the one or more indicators 116 is provided for illustrative purposes only. It should be appreciated that other quantities of the one or more indicators 116 and other colors of light are contemplated.

In response to the actuator component 124 actuating when the sensor component 118 moves from the first position to the second position, the first indicator may emit a first color of light. In response to the actuator component 124 actuating when the sensor component 118 moves from the first position to the third position, the second indicator may emit a second color of light. In response to the actuator component 124 actuating when the sensor component 118 moves from the first position to the fourth position, the third indicator may emit a third color of light.

In further examples, the alarm assembly 114 may comprise one or more components or buttons, such as buttons 148 of FIG. 2, to indicate an on status of the alarm assembly 114, an off status of the alarm assembly 114, a low power status of the battery 110, and a silent mode for the alarm assembly 114.

In a further example, in response to the actuator component 124 actuating when the sensor component 118 moves from the first position to the second position, a first message (e.g., that the movement of the tracheostomy tube 106 is of low priority) may be portrayed via the display 142 of the alarm assembly 114. In response to the actuator component 124 actuating when the sensor component 118 moves from the first position to the third position, a second message may be portrayed via the display 142 of the alarm assembly 114. In response to the actuator component 124 actuating when the sensor component 118 moves from the first position to the fourth position, a third message (e.g., that the movement of the tracheostomy tube 106 is of high priority) may be portrayed via the display 142 of the alarm assembly 114.

Each of the first, second, and third messages may differ. Further, each of the first, second, and third messages may contain images (e.g., an exclamation point indicating a large movement of the tracheostomy tube 106 and a high priority), letters (e.g., "low movement," "high movement," etc.), and/or numbers (e.g., a number of three for large movement of the tracheostomy tube 106 and a high priority or a number of one for a slight movement of the tracheostomy tube 106 and a low priority).

It should be appreciated that the device 104 is configured to communicate with and/or transmit data to another device, such as the mobile device 128 via Wi-Fi, Bluetooth, Bluetooth Low Energy (Bluetooth LE), or near-field communication (NFC). More specifically, the transmitter 140 of the alarm assembly 114 of the device 104 is configured to transmit an audio signal and/or a visual signal via the network 126 (such as the Internet) to the mobile device 128 (e.g., the electronic device) in response to the production of the alert.

The mobile device 128 may be: a computer, a laptop computer, a smartphone, a tablet, a base station, an intercom system, a board alarm, and/or a remote station, among other examples not explicitly listed herein. The mobile device 128 may be associated with a user 138, such as a medical personnel, such as a doctor, a nurse, or a caregiver. Moreover, as depicted in FIG. 1, the mobile device 128 may have numerous components, such as a memory 132, a display 134, a processor 136, and/or an application 130. The components of the mobile device 128 will be discussed in greater detail herein.

Wireless LANs (WLANs) in which a mobile user can connect to a local area network (LAN) through a wireless connection may be employed for wireless communications. Wireless communications can include communications that propagate via electromagnetic waves, such as light, infrared, radio, and microwave. There are a variety of WLAN standards that currently exist, such as Bluetooth®, Bluetooth LE, and IEEE 802.11.

By way of example, Bluetooth products may be used to provide links between mobile computers, mobile phones, portable handheld devices, personal digital assistants (PDAs), and other mobile devices and connectivity to the Internet. Bluetooth is a computing and telecommunications industry specification that details how mobile devices can easily interconnect with each other and with non-mobile devices using a short-range wireless connection. Bluetooth creates a digital wireless protocol to address end-user problems arising from the proliferation of various mobile devices that need to keep data synchronized and consistent from one device to another, thereby allowing equipment from different vendors to work seamlessly together.

Figure 8:
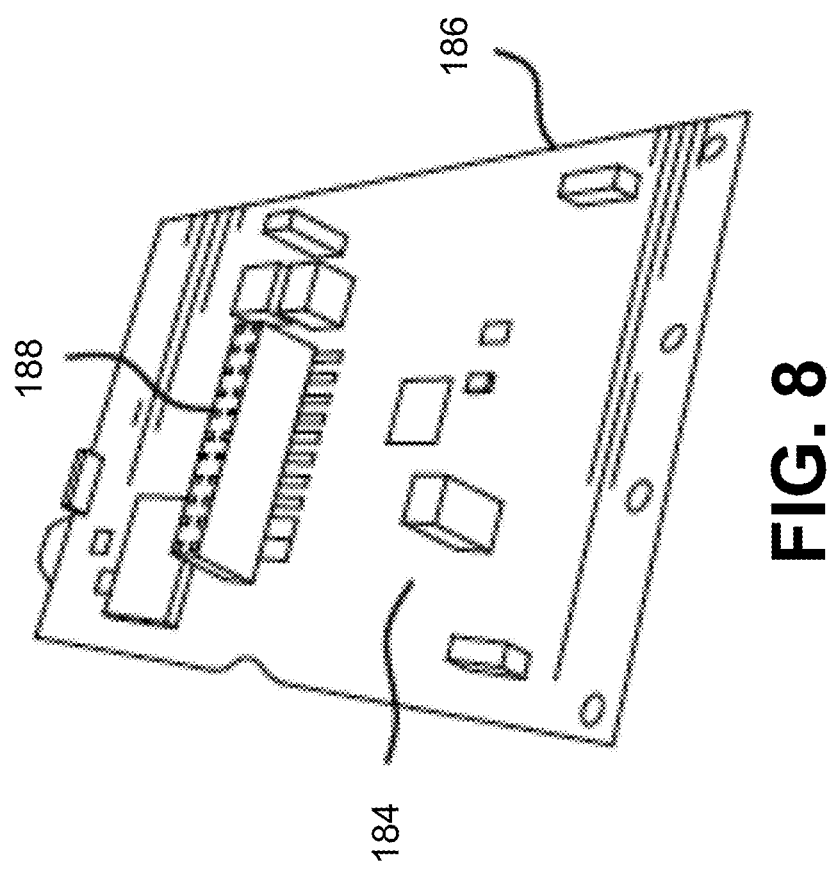
FIG. 8 depicts a perspective view of a launch pad for use with a device, according to at least some embodiments disclosed herein.
Figure 9:
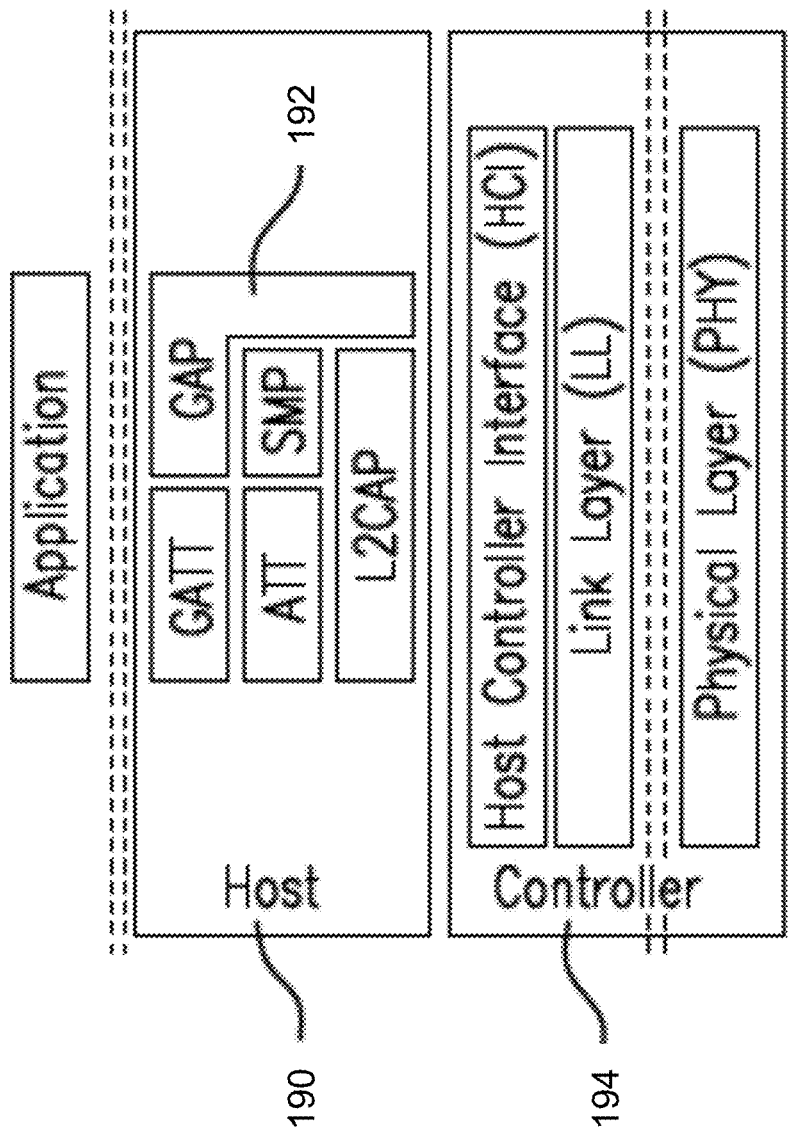
FIG. 9 depicts a block diagram of a Bluetooth Protocol Stack for use with a device, according to at least some embodiments disclosed herein.
Figure 10:
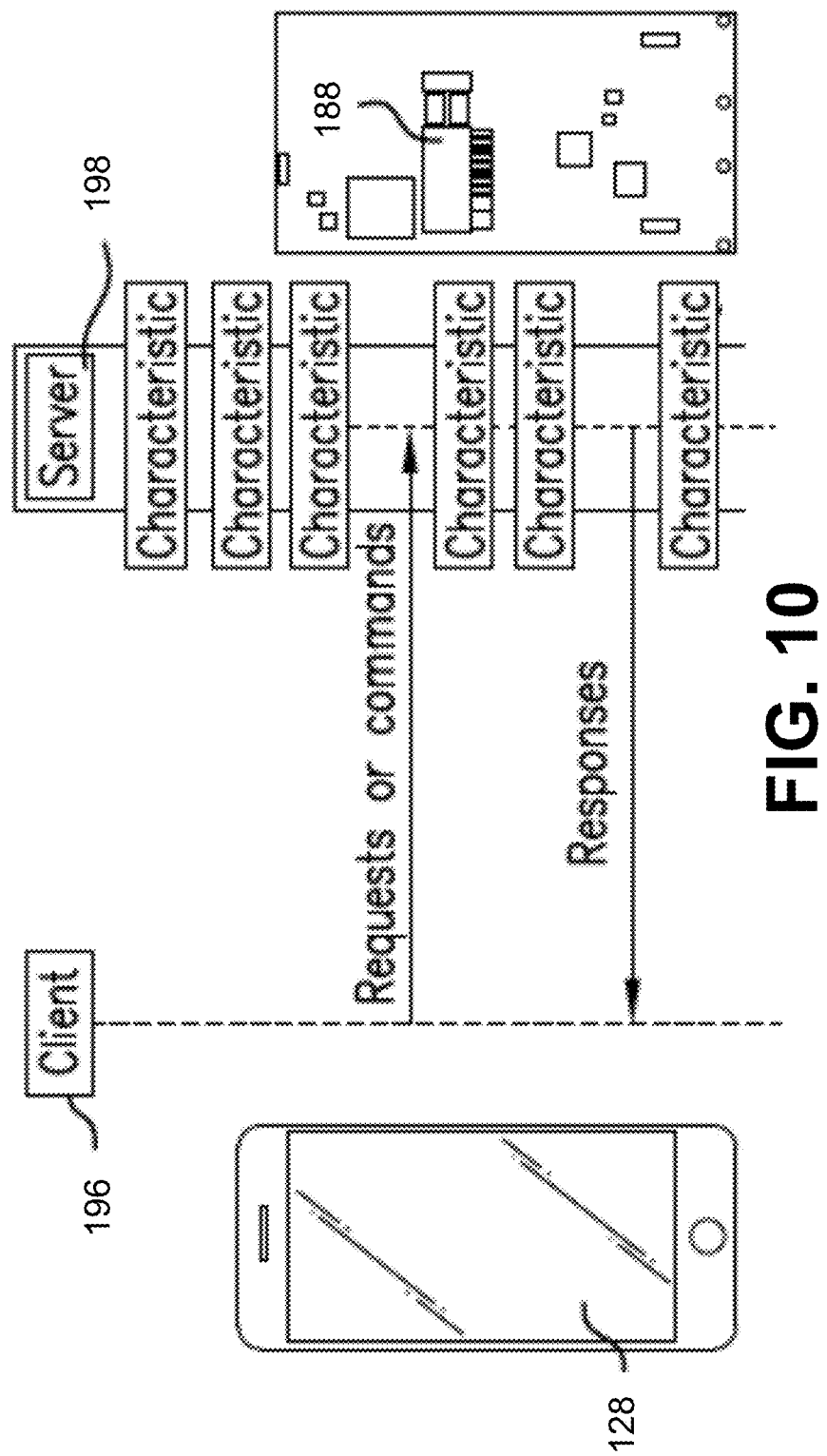
FIG. 10 depicts a block diagram of a system, according to at least some embodiments disclosed herein.

As shown in FIG. 9, the Bluetooth Protocol Stack consists of layers of software abstractions from the user application interfaces with a Generic Attribute Profile (GATT) layer 190 using an Application Program Interface (API) to provide services and characteristics. The Bluetooth Protocol Stack of FIG. 9 also has a bottom physical layer being a controller 194 that interfaces with the radio transmission hardware. A Generic Access Profile (GAP) 192 provides connection functionality between a server 198 and a client 196 (of FIG. 10). More specifically, FIG. 10 depicts the client-server connection between the mobile device 128 and the microcontroller (e.g., launchpad development board). FIG. 8 also depicts a booster pack 188.

An IEEE standard, IEEE 802.11, specifies technologies for wireless LANs and devices. Using 802.11, wireless networking may be accomplished with each single base station supporting several devices. In some examples, devices may come pre-equipped with wireless hardware or a user may install a separate piece of hardware, such as a card, that may include an antenna. By way of example, devices used in 802.11 typically include three notable elements, whether or not the device is an access point (AP), a mobile station (STA), a bridge, a personal computing memory card International Association (PCMCIA) card (or PC card) or another device: a radio transceiver; an antenna; and a MAC (Media Access Control) layer that controls packet flow between points in a network.

As described herein, "NFC" is a set of communication protocols for communication between two electronic devices over a distance of 4 cm or less. NFC devices can act as electronic identity documents and keycards and may be used in contactless payment systems and allow mobile payment replacing or supplementing systems such as credit cards and electronic ticket smart cards. NFC can be used for sharing small files such as contacts, and bootstrapping fast connections to share larger media such as photos, videos, and other files.

Figure 7:
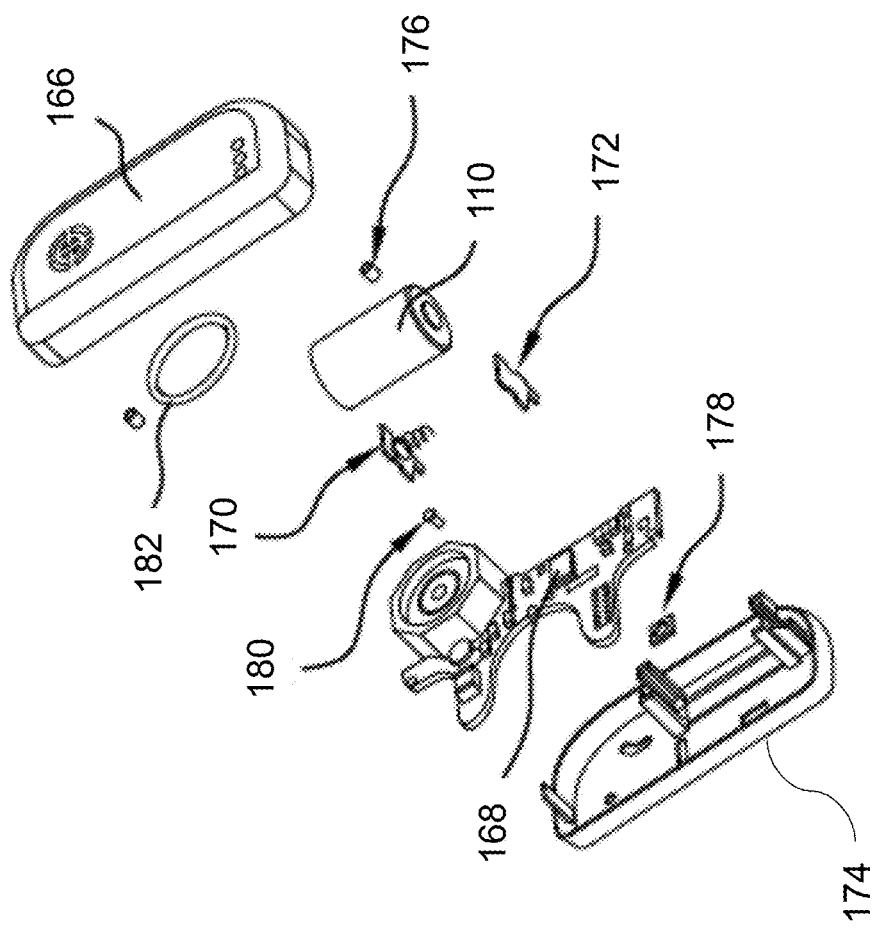
FIG. 7 depicts an exploded view of an alarm assembly of a device, according to at least some embodiments disclosed herein.

In a preferred embodiment, and as depicted in FIG. 7, the alarm assembly 114 includes a top housing 166 and a bottom housing 174, each of which form a waterproof unit. The alarm assembly 114 includes numerous internal components, such as a connected PCB assembly 168, a battery (such as the battery 110), a positive contact 170, a negative contact 172, firmware, software, an adhesive sheeting 178, a screw 180 (such as a PCB screw), and/or a seal 182 (such as an O-ring). The battery 110 may be a lithium battery, in examples. In other examples, the battery 110 may be a CR2 battery ultra-lithium. One or more securement components 176 may also be used to affix the top housing 166 to the bottom housing 174 to form the waterproof unit, with the internal components being disposed therein. In examples, the one or more securement components 176 may comprise screws or threaded screws. More specifically, the one or more securement components 176 may be threaded inserts. In some examples, the adhesive sheeting 178 may be adhesive silicone sheeting. Further, the seal 182 may be a silicone O-ring.

In an example, and as depicted in FIG. 8, the software of FIG. 7 includes a development board 184 for a launchpad 186, that contains one or more microcontrollers and provides functionality for the device 104. In some examples, the development board 184 for the launchpad 186 contains three microcontrollers and the booster pack 188. However, it should be appreciated that a quantity of the microcontrollers is not limited to any particular quantity. The microcontrollers are used to detect separation of the tracheostomy tube 106 from the trachea of the patient 102, interface with the sensor component 118, and provide wireless communication capabilities to the mobile device 128.

A method to detect movement of the tracheostomy tube 108 is also described herein. The method includes numerous process steps, such as: affixing the tracheostomy tube 106 to the patient 102 and attaching the device 104 to the patient 102. The device 104 is configured to prevent movement of the tracheostomy tube 106. The device 104 comprises the faceplate 122 and the tracheostomy collar 108. The tracheostomy collar 108 includes the actuator component 124 and the sensor component 118 located proximate the faceplate 122. The tracheostomy collar 108 also includes the alarm assembly 114 and the transmitter 140.

In response to detecting movement, by the sensor component 118, from a first position to a second position, from the first position to a third position, and from the first position to a fourth position, the method further includes the actuator component 124 actuating. The first position, the second position, the third position, and the fourth position differ. Further, the second position is further from the actuator component 124 than the first position. The third position is further from the actuator component 124 than the first position and the second position. Additionally, the fourth position is further from the actuator component 124 than the first position, the second position, and the third position.

The method further includes: transmitting, by the sensor component 118, a signal to the alarm assembly 114 in response to the actuation of the actuator component 124; producing, by the alarm assembly 114, the alert in response to receiving the signal from the sensor component 118; and transmitting, by the transmitter 140, the alert to the mobile device 128 via the network 126.

Figure 15:
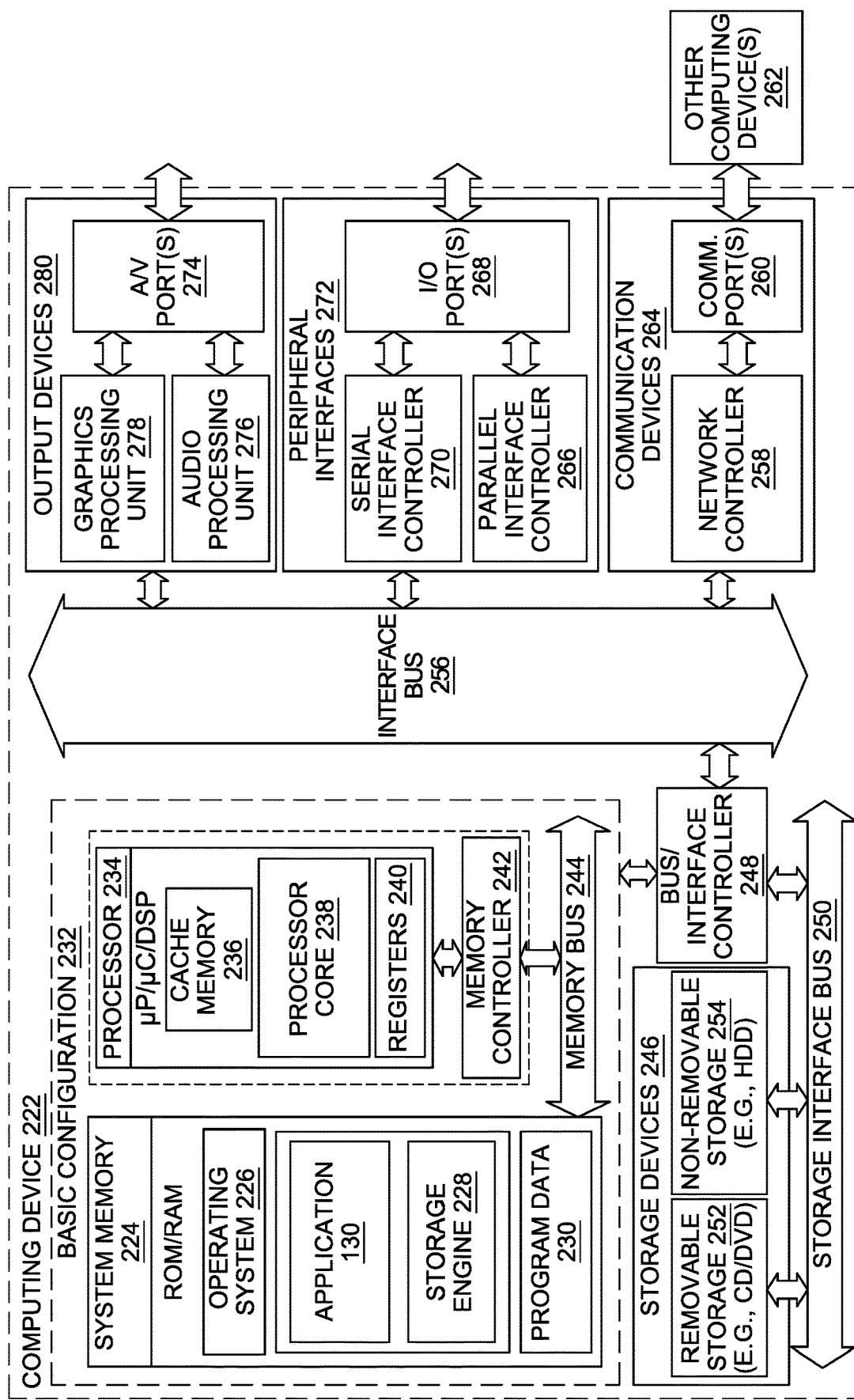
FIG. 15 depicts a block diagram of a computing device to be used with at least the system of FIG. 1, according to at least some embodiments disclosed herein.

FIG. 15 is a block diagram of a computing/mobile device included within the computer system of FIG. 1. In some embodiments, the mobile device 128 (of FIG. 1) or the computing device 222 (of FIG. 15) may be utilized to implement one or more methods.

A basic configuration 232 of a computing device 222 is illustrated in FIG. 15 by those components within the inner dashed line. In the basic configuration 232 of the computing device 222, the computing device 222 includes a processor 234 and a system memory 224. In some examples, the computing device 222 may include one or more processors and the system memory 224. A memory bus 244 is used for communicating between the one or more processors 234 and the system memory 224.

Depending on the desired configuration, the processor 234 may be of any type, including, but not limited to, a microprocessor (μP), a microcontroller (μC), and a digital signal processor (DSP), or any combination thereof. Further, the processor 234 may include one more levels of caching, such as a level cache memory 236, a processor core 238, and registers 240, among other examples. The processor core 238 may include an arithmetic logic unit (ALU), a floating point unit (FPU), and/or a digital signal processing core (DSP Core), or any combination thereof. A memory controller 242 may be used with the processor 234, or, in some implementations, the memory controller 242 may be an internal part of the memory controller 242.

Depending on the desired configuration, the system memory 224 may be of any type, including, but not limited to, volatile memory (such as RAM), and/or non-volatile memory (such as ROM, flash memory, etc.), or any combination thereof. The system memory 224 includes an operating system 226, one or more engines, the application 130, and program data 230. In some embodiments, the application 130 may be an engine, a software program, a service, or a software platform, as described infra. The system memory 224 may also include a storage engine 228 that may store any information disclosed herein.

The second user 138 may engage with the application 130 of the mobile device 128 or the computing device 222 to monitor movement of the tracheostomy tube 108. The application 130 may receive the alert from the transmitter 124 of the alarm assembly 114 of the tracheostomy collar 104. In the case of a visual alert, such alert may be displayed via to the display 134 to the second user 138. In the case of an audio alert, such alert may be projected by the speaker of the mobile device 128.

Moreover, the computing device 222 may have additional features or functionality, and additional interfaces to facilitate communications between the basic configuration 232 and any desired devices and interfaces. For example, a bus/interface controller 248 is used to facilitate communications between the basic configuration 232 and data storage devices 246 via a storage interface bus 250. The data storage devices 246 may be one or more removable storage devices 252, one or more non-removable storage devices 254, or a combination thereof. Examples of the one or more removable storage devices 252 and the one or more non-removable storage devices 254 include magnetic disk devices (such as flexible disk drives and hard-disk drives (HDD)), optical disk drives (such as compact disk (CD) drives or digital versatile disk (DVD) drives), solid state drives (SSD), and tape drives, among others.

In some embodiments, an interface bus 256 facilitates communication from various interface devices (e.g., one or more output devices 280, one or more peripheral interfaces 272, and one or more communication devices 264) to the basic configuration 232 via the bus/interface controller 256. Some of the one or more output devices 280 include a graphics processing unit 278 and an audio processing unit 276, which are configured to communicate to various external devices, such as a display or speakers, via one or more A/V ports 274.

The one or more peripheral interfaces 272 may include a serial interface controller 270 or a parallel interface controller 266, which are configured to communicate with external devices, such as input devices (e.g., a keyboard, a mouse, a pen, a voice input device, or a touch input device, etc.) or other peripheral devices (e.g., a printer or a scanner, etc.) via one or more I/O ports 268.

Further, the one or more communication devices 264 may include a network controller 258, which is arranged to facilitate communication with one or more other computing devices 262 over a network communication link via one or more communication ports 260. The one or more other computing devices 262 include servers, the database, mobile devices, and comparable devices.

The network communication link is an example of a communication media. The communication media are typically embodied by the computer-readable instructions, data structures, program modules, or other data in a modulated data signal, such as a carrier wave or other transport mechanism, and include any information delivery media. A "modulated data signal" is a signal that has one or more of its characteristics set or changed in such a manner as to encode information in the signal. By way of example, and not limitation, the communication media may include wired media (such as a wired network or direct-wired connection) and wireless media (such as acoustic, radio frequency (RF), microwave, infrared (IR), and other wireless media). The term "computer-readable media," as used herein, includes both storage media and communication media.

It should be appreciated that the system memory 224, the one or more removable storage devices 252, and the one or more non-removable storage devices 254 are examples of the computer-readable storage media. The computer-readable storage media is a tangible device that can retain and store instructions (e.g., program code) for use by an instruction execution device (e.g., the computing device 222). Any such, computer storage media is part of the computing device 222.

The computer readable storage media/medium can be a tangible device that can retain and store instructions for use by an instruction execution device. The computer readable storage media/medium may be, for example, but is not limited to, an electronic storage device, a magnetic storage device, an optical storage device, an electromagnetic storage device, and/or a semiconductor storage device, or any suitable combination of the foregoing. A non-exhaustive list of more specific examples of the computer readable storage media/medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and/or a mechanically encoded device (such as punch-cards or raised structures in a groove having instructions recorded thereon), and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Aspects of the present invention are described herein regarding illustrations and/or block diagrams of methods, computer systems, and computing devices according to embodiments of the invention. It will be understood that each block in the block diagrams, and combinations of the blocks, can be implemented by the computer-readable instructions (e.g., the program code).

The computer-readable instructions are provided to the processor 234 of a general purpose computer, special purpose computer, or other programmable data processing apparatus (e.g., the computing device 222) to produce a machine, such that the instructions, which execute via the processor 234 of the computer or other programmable data processing apparatus, create means for implementing the functions/acts specified in the block diagram blocks. These computer-readable instructions are also stored in a computer-readable storage medium that can direct a computer, a programmable data processing apparatus, and/or other devices to function in a particular manner, such that the computer-readable storage medium having instructions stored therein comprises an article of manufacture including instructions, which implement aspects of the functions/acts specified in the block diagram blocks.

The computer-readable instructions (e.g., the program code) are also loaded onto a computer (e.g. the computing device 222), another programmable data processing apparatus, or another device to cause a series of operational steps to be performed on the computer, the other programmable apparatus, or the other device to produce a computer implemented process, such that the instructions, which execute on the computer, the other programmable apparatus, or the other device, implement the functions/acts specified in the block diagram blocks.

Computer readable program instructions described herein can also be downloaded to respective computing/processing devices from a computer readable storage medium or to an external computer or external storage device via a network (e.g., the Internet, a local area network, a wide area network, and/or a wireless network). The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer/computing device, partly on the user's computer/computing device, as a stand-alone software package, partly on the user's computer/computing device and partly on a remote computer/computing device or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to block diagrams of methods, computer systems, and computing devices according to embodiments of the invention. It will be understood that each block and combinations of blocks in the diagrams, can be implemented by the computer readable program instructions.

The block diagrams in the Figures illustrate the architecture, functionality, and operation of possible implementations of computer systems, methods, and computing devices according to various embodiments of the present invention. In this regard, each block in the block diagrams may represent a module, a segment, or a portion of executable instructions for implementing the specified logical function (s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block and combinations of blocks can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others or ordinary skill in the art to understand the embodiments disclosed herein.

When introducing elements of the present disclosure or the embodiments thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A device configured to monitor movement of a tracheostomy tube, the device comprising:
    a faceplate comprising:
        a portion, the portion having a first opening configured to receive the tracheostomy tube, the portion having a first side disposed opposite a second side, each of the first side and second side of the portion having a tracheostomy collar opening which is above the first opening;
        a body, the body overlays the portion, the body comprising second opening disposed therethrough, wherein the second opening receives a portion of the tracheostomy tube therein; and
        a first end disposed opposite a second end, the first end of the faceplate comprising a first aperture and the second end of the faceplate comprising a second aperture; and
    a tracheostomy collar comprising:
        a main body having a first end and a second end, the first end of the tracheostomy collar having a first fastener, the first fastener passes through both the first aperture of the body of the faceplate and tracheostomy collar opening of the first side of the portion and the second end of the tracheostomy collar having a second fastener, the second fastener passes through both the second aperture of the body of the faceplate and tracheostomy collar opening of the second side of the portion;
        a sensor component and an actuator component each located proximate the faceplate, the actuator component being configured to actuate when the sensor component detects movement of the tracheostomy tube being moved from a first position to a second position, from the first position to a third position, and from the first position to a fourth position,
        wherein the first position, the second position, the third position, and the fourth position differ,
        wherein the second position of the tracheostomy tube is farther from the actuator component than the first position of the tracheostomy tube,
        wherein the third position of the tracheostomy tube is farther from the actuator component than the first position of the tracheostomy tube and the second position of the tracheostomy tube, and
        wherein the fourth position of the tracheostomy tube is farther from the actuator component than the first position of the tracheostomy tube, the second position of the tracheostomy tube, and the third position of the tracheostomy tube;
    the sensor component being configured to transmit a signal to an alarm assembly in response to the actuator component actuating; and
    the alarm assembly being configured to produce an alert in response to receiving the signal from the sensor component.

2. The device of claim 1, wherein the alarm assembly comprises:
    an alarm circuitry; and
    a battery.

3. The device of claim 1, wherein the alarm assembly comprises:
    a transmitter configured to transmit at least one of an audio signal and a visual signal to an electronic device in response to the production of the alert.

4. The device of claim 1, wherein the alarm assembly comprises:
    a speaker configured to produce an audio alert in response to the production of the alert.

5. The device of claim 1, wherein the alarm assembly comprises one or more indicators.

6. The device of claim 5, wherein each of the one or more indicators comprise a light-emitting diode (LED).

7. The device of claim 5, wherein a first indicator of the one or more indicators emits a first color of light, wherein a second indicator of the one or more indicators emits a second color of light, and wherein a third indicator of the one or more indicators emits a third color of light.

8. The device of claim 7, wherein the first color of light, the second color of light, and the third color of light differ.

9. The device of claim 7, wherein, in response to the actuator component actuating when the sensor component detects movement of the tracheostomy tube being moved from the first position to the second position, the first indicator emits the first of light.

10. The device of claim 7, wherein, in response to the actuator component actuating when the sensor component detects movement of the tracheostomy tube being moved from the first position to the third position, the second indicator emits the second of light.

11. The device of claim 7, wherein, in response to the actuator component actuating when the sensor component detects movement of the tracheostomy tube being moved from the first position to the fourth position, the third indicator emits the third of light.

12. A system to monitor movement of a tracheostomy tube, the system comprising:
    a network;

an electronic device; and a device configured to prevent movement of the tracheostomy tube, the device comprising: a faceplate comprising:
- a portion, the portion having a first opening configured to receive the tracheostomy tube, the portion having a first side disposed opposite a second side, each of the first side and second side of the portion having a tracheostomy collar opening which is above the first opening;
- a body, the body overlays the portion, comprising a second opening disposed therethrough, wherein the second opening receives a portion of the tracheostomy tube therein; and a first end disposed opposite a second end, the first end of the faceplate comprising a first aperture and the second end of the faceplate comprising a second aperture; and
- a tracheostomy collar comprising:
- a main body having a first end and a second end, the first end of the tracheostomy collar having a first fastener, the first fastener passes through both the first aperture of the body of the faceplate and tracheostomy collar opening of the first side of the portion and the second end of the tracheostomy collar having a second fastener, the second fastener passes through both the second aperture of the body of the faceplate and tracheostomy collar opening of the second side of the portion;
- a sensor component and an actuator component each located proximate the faceplate;
- the sensor component being configured to transmit a signal to an alarm assembly in response to the actuator component actuating; and
- the alarm assembly being configured to produce an alert in response to receiving the signal from the sensor component.

13. The system of claim 12, wherein the alarm assembly further comprises:
a speaker configured to produce an audio alert in response to the production of the alert.

14. The system of claim 12, wherein the alarm assembly further comprises:
one or more indicators, wherein each of the one or more indicators comprise a light-emitting diode (LED).

15. The system of claim 14, wherein a first indicator of the one or more indicators emits a first color of light, wherein a second indicator of the one or more indicators emits a second color of light, wherein a third indicator of the one or more indicators emits a third color of light,
wherein the first color of light, the second color of light, and the third color of light differ.

16. The system of claim 15, wherein, in response to the actuator component actuating when the sensor component detects movement of the tracheostomy tube being moved from a first position to a second position, the first indicator emits the first color of light, in response to the actuator component actuating when the sensor component detects movement of the tracheostomy tube being moved from the first position to a third position, the second indicator emits the second color of light, and in response to the actuator component actuating when the sensor component detects movement of the tracheostomy tube being moved from the first position to a fourth position, the third indicator emits the third color of light.

17. A method to monitor movement of a tracheostomy tube, the method comprising:
affixing the tracheostomy tube to a patient;
attaching a device to the patient, the device is configured to detect movement of the tracheostomy tube, wherein the device comprises a faceplate and a tracheostomy collar, and wherein
the faceplate comprising a portion, the portion having a first opening configured to receive the tracheostomy tube, the portion having a first side disposed opposite a second side, each of the first side and second side of the portion having a tracheostomy collar opening which is above the first opening; and wherein
the tracheostomy collar comprises:
a main body having a first end and a second end, the first end of the tracheostomy collar having a first fastener, the first fastener passes through both the first aperture of the body of the faceplate and tracheostomy collar opening of the first side of the portion and the second end of the tracheostomy collar having a second fastener, the second fastener passes through both the second aperture of the body of the faceplate and tracheostomy collar opening of the second side of the portion;
an actuator component and a sensor component located proximate the faceplate; an alarm assembly; and
a transmitter;
in response to detecting movement of the tracheostomy tube, the sensor component transmits a signal to an alarm assembly in response to the actuation of the actuator component, wherein the alarm assembly further comprises one or more indicators, wherein each of the one or more indicators comprise a light-emitting diode (LED), wherein in response to the actuator component actuating when the sensor component detects movement of the tracheostomy tube being moved from a first position to a second position, a first indicator of the one or more indicators emits a first color of light, in response to the actuator component actuating when the sensor component detects movement of the tracheostomy tube being moved from the first position to a third position, a second indicator of the one or more indicators emits a second color of light, and
in response to the actuator component actuating when the sensor component detects movement of the tracheostomy tube being moved from the first position to a fourth position, a third indicator of the one or more indicators emits a third color of light;
the alarm assembly configured to produce an alert in response to receiving the signal from the sensor component; and
the transmitter configured to transmit the alert to an electronic device via a network.

18. The method of claim 17, wherein the first color of light, the second color of light, and the third color of light differ.

* * * * *